United States Patent
Mak et al.

(10) Patent No.: US 11,172,823 B2
(45) Date of Patent: Nov. 16, 2021

(54) METHOD, SYSTEM AND APPARATUS FOR TRACKING SURGICAL IMAGING DEVICES

(71) Applicant: SYNAPTIVE MEDICAL INC., Toronto (CA)

(72) Inventors: Siu Wai Jacky Mak, Toronto (CA); Michael Frank Gunter Wood, Toronto (CA); Thanh Vinh Vuong, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 37 days.

(21) Appl. No.: 15/514,374

(22) PCT Filed: Mar. 17, 2015

(86) PCT No.: PCT/CA2015/000163
§ 371 (c)(1),
(2) Date: Mar. 24, 2017

(87) PCT Pub. No.: WO2016/145506
PCT Pub. Date: Sep. 22, 2016

(65) Prior Publication Data
US 2017/0296293 A1 Oct. 19, 2017

(51) Int. Cl.
*A61B 5/00* (2006.01)
*A61B 5/055* (2006.01)
(Continued)

(52) U.S. Cl.
CPC ............ *A61B 5/0066* (2013.01); *A61B 5/055* (2013.01); *A61B 5/7425* (2013.01); *A61B 34/20* (2016.02);
(Continued)

(58) Field of Classification Search
CPC . G06T 2207/10101; G06T 2207/10088; G06T 7/0012; G06F 19/3481;
(Continued)

(56) References Cited

U.S. PATENT DOCUMENTS 5,643,296 A * 7/1997 Hundertmark ..... A61B 17/3207
604/22
6,725,077 B1 * 4/2004 Balloni .................. A61B 5/055
600/410
(Continued)

FOREIGN PATENT DOCUMENTS

EP 2676627 A2 12/2013

OTHER PUBLICATIONS

International Preliminary Report on Patentability dated Feb. 22, 2017 for PCT International Application No. PCT/CA2015/000163.
(Continued)

*Primary Examiner* — Keith M Raymond
*Assistant Examiner* — Helene Bor (57) ABSTRACT

A computing device for tracking surgical imaging devices stores a preoperative image of patient tissue registered to a frame of reference of a tracking system; and receives, from a first imaging device, a first intraoperative image of a first region of the tissue, with a finer resolution than the preoperative image. The computing device receives a position of the first imaging device from the tracking system, and registers the first intraoperative image with the frame of reference. The computing device receives, from a second imaging device, a second intraoperative image of a second region of the patient tissue, with a finer resolution than the first intraoperative image. The computing device registers the second intraoperative image to the first intraoperative image; and controls a display to present the preoperative image overlaid with the first intraoperative image, and the
(Continued)

first intraoperative image overlaid with the second intraoperative image.

20 Claims, 10 Drawing Sheets

(51) Int. Cl.
G16H 20/40 (2018.01)
G16H 30/40 (2018.01)
A61B 34/20 (2016.01)
A61B 90/00 (2016.01)
G06T 7/00 (2017.01)

(52) U.S. Cl.
CPC ............ *A61B 90/37* (2016.02); *G06T 7/0012* (2013.01); *G16H 20/40* (2018.01); *G16H 30/40* (2018.01); *A61B 5/0095* (2013.01); *A61B 2034/2065* (2016.02); *A61B 2090/374* (2016.02); *A61B 2090/3735* (2016.02); *G06T 2207/10088* (2013.01); *G06T 2207/10101* (2013.01)

(58) Field of Classification Search
CPC ................ G06F 19/321; A61B 5/7425; A61B 2090/374; A61B 2090/3735; A61B 5/055; A61B 5/0066; A61B 90/37
See application file for complete search history.

(56) References Cited

U.S. PATENT DOCUMENTS

| | | | | |
|---|---|---|---|---|
| 6,873,867 B2* | 3/2005 | Vilsmeier | ............. | A61B 90/36 600/415 |
| 7,693,349 B2 | 4/2010 | Gering | | |
| 7,930,014 B2* | 4/2011 | Huennekens | .......... | A61B 6/504 382/159 |
| 2001/0016684 A1* | 8/2001 | Shahidi | .................. | A61B 34/20 600/429 |
| 2001/0055062 A1* | 12/2001 | Shioda | ............... | A61B 1/00039 348/79 |
| 2003/0069471 A1* | 4/2003 | Nakanishi | ............ | A61B 1/0005 600/101 |
| 2006/0098897 A1 | 5/2006 | Dewaele | | |
| 2006/0267977 A1 | 11/2006 | Barfuss et al. | | |
| 2007/0225553 A1* | 9/2007 | Shahidi | .................. | A61B 8/12 600/103 |
| 2008/0089566 A1* | 4/2008 | Node-Langlois | ......... | G06T 7/30 382/128 |
| 2008/0119712 A1* | 5/2008 | Lloyd | .................... | A61B 90/36 600/407 |
| 2009/0132285 A1* | 5/2009 | Jakobovits | ............ | G06F 3/0482 705/3 |
| 2009/0287505 A1* | 11/2009 | Wood | ..................... | G06Q 50/22 705/3 |
| 2010/0331782 A1* | 12/2010 | Hendriks | ............. | A61B 5/0066 604/164.12 |
| 2012/0059251 A1* | 3/2012 | Bakker | ................. | A61B 5/0062 600/424 |
| 2012/0134562 A1 | 5/2012 | Boettger et al. | | |
| 2016/0067007 A1* | 3/2016 | Piron | .................. | A61B 5/7246 705/3 |

OTHER PUBLICATIONS

International Search Report dated Nov. 5, 2015 for International Application No. PCT/CA2015/000163.
Written Opinion dated Nov. 5, 2015 for International Application No. PCT/CA2015/000163.

\* cited by examiner

METHOD, SYSTEM AND APPARATUS FOR TRACKING SURGICAL IMAGING DEVICES

FIELD

The specification relates generally to tracking surgical instruments, and specifically to a method, system and apparatus for tracking surgical imaging devices.

BACKGROUND

Medical procedures, such as brain surgery, are sometimes performed with the aid of tracking systems to indicate (e.g. on a display) where various surgical instruments are located relative to the patient. Such tracking systems can include reflective markers on the instruments themselves, which are detected by one or more cameras. For example, an imaging device may be equipped with markers visible to tracking cameras, and with the help of tracking information the images of the patient captured by that device can be overlaid on a larger, preoperative image of the patient on a display.

Conventional tracking systems, however have limited resolutions. Certain imaging devices are capable of capturing high-resolution images of small areas of the patient (sometimes smaller than the resolution of the tracking system). Novel surgical tools or effectors may be capable of affecting the surgical area down to the cellular level. The tracking system may not be capable of tracking such imaging devices and tools with sufficient accuracy to correctly represent the location of the high-resolution images on the preoperative image. In other words, it may become difficult or impossible to clearly indicate on a display exactly which portion of the patient is being observed or affected with the high-resolution images.

SUMMARY

According to an aspect of the specification, a method of tracking surgical imaging devices using a computing device is provided, comprising: storing a preoperative image of patient tissue registered to a frame of reference of a tracking system connected to the computing device; receiving, from a first imaging device, a first intraoperative image of a first region of the patient tissue; the first intraoperative image having a finer resolution than the preoperative image; receiving a position of the first imaging device in the frame of reference from the tracking system, and registering the first intraoperative image with the frame of reference based on the position; receiving, from a second imaging device, a second intraoperative image of a second region of the patient tissue; the second region being smaller than the first region and the second intraoperative image having a finer resolution than the first intraoperative image; registering the second intraoperative image to the first intraoperative image; and controlling a display connected to the computing device to present the preoperative image overlaid with the first intraoperative image, and the first intraoperative image overlaid with the second intraoperative image.

According to another aspect of the specification, a computing device for tracking surgical imaging devices is provided. The computing device comprises: a display; a memory storing a preoperative image of patient tissue registered to a frame of reference of a tracking system connected to the computing device; a processor interconnected with the memory and the display, the processor configured to: receive, from a first imaging device, a first intraoperative image of a first region of the patient tissue; the first intraoperative image having a finer resolution than the preoperative image; receive a position of the first imaging device in the frame of reference from the tracking system, and register the first intraoperative image with the frame of reference based on the position; receive, from a second imaging device, a second intraoperative image of a second region of the patient tissue; the second region being smaller than the first region and the second intraoperative image having a finer resolution than the first intraoperative image; register the second intraoperative image to the first intraoperative image; and control the display to present the preoperative image overlaid with the first intraoperative image, and the first intraoperative image overlaid with the second intraoperative image.

BRIEF DESCRIPTIONS OF THE DRAWINGS

Embodiments are described with reference to the following figures, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

Unless defined otherwise, all technical and scientific terms used herein are intended to have the same meaning as commonly understood to one of ordinary skill in the art. Unless otherwise indicated, as used herein, the following terms are intended to have the following meanings:

As used herein the term "intraoperative" refers to an action, process, method, event or step that occurs or is carried out during at least a portion of a medical procedure. The term "preoperative" as used herein refers to an action, process, method, event or step that occurs or is carried out before the medical procedure begins. The terms intraoperative and preoperative, as defined herein, are not limited to surgical procedures, and may refer to other types of medical procedures, such as diagnostic and therapeutic procedures.

Figure 1:
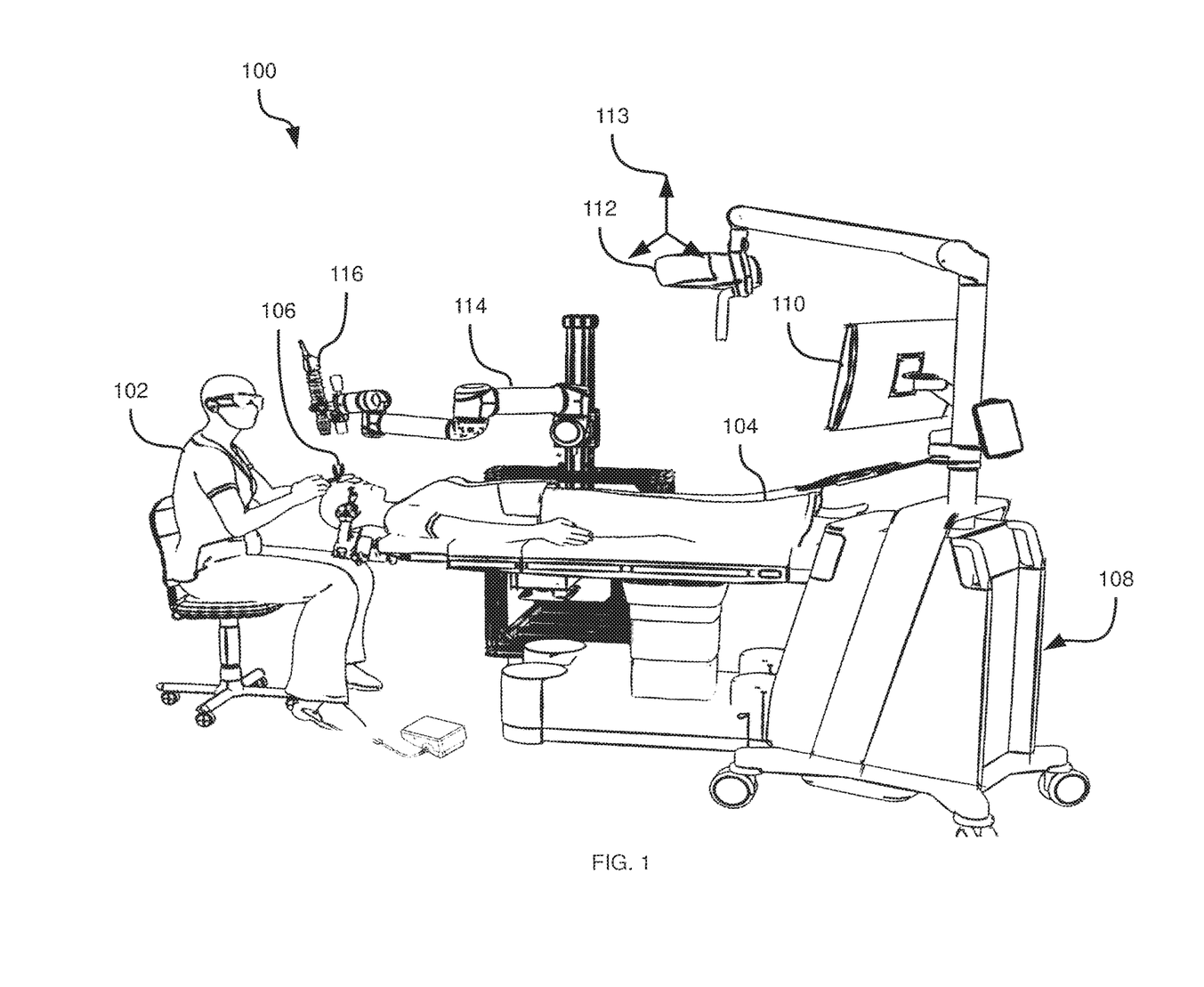
FIG. 1 depicts an operating theatre, according to a non-limiting embodiment.

FIG. 1 depicts a surgical operating theatre 100 in which a healthcare worker 102 (e.g. a surgeon) operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. The description below makes reference to the brain of patient 104 as an example of tissue to which the techniques herein may be applied. It will be understood, however, that those techniques may also be applied to a wide variety of other tissues. Thus, when the brain of patient 104 is mentioned below, it is simply an example of the various tissues in connection with which the systems and methods herein may be implemented.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer (not shown) is generally inserted into access port 106. The introducer is typically a cylindrical device that slidably engages the internal surface of access port 106 and bears a conical atraumatic tip to allow for insertion of access port 106 into the sulcal folds of the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like. Additional instruments may be employed to conduct the procedure that do not extend into access port 106, such as laser ablation devices (which can emit laser light into access port 106).

Also shown in FIG. 1 is an equipment tower 108 supporting a computing device (not shown) such as a desktop computer, as well as one or more displays 110 connected to the computing device for displaying images provided by the computing device.

Equipment tower 108 also supports a tracking system 112. Tracking system 112 is generally configured to track the positions of one or more reflective markers (not shown) mounted on access port 102, any of the above-mentioned surgical tools and instruments, or any combination thereof. Such markers, also referred to as fiducial markers, may also be mounted on patient 104, for example at various points on patient 104's head. Tracking system 112 may therefore include a camera (e.g. a stereo camera) and a computing device (either the same computing device as mentioned above or a separate computing device) configured to locate the fiducial markers in the images captured by the camera, and determine the spatial positions of those markers within the operating theatre. The spatial positions may be provided by tracking system 112 to the computing device in equipment tower 108 for subsequent use. The positions determined by tracking system 112 may be provided in a frame of reference 113 (that is, a coordinate system) centered at a point of origin within the operating room.

The nature of the markers and the camera are not particularly limited. For example, the camera may be sensitive to infrared (IR) or near-infrared (NIR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or unpulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. The predefined locations, as well as the geometry of each tracked object, are configured within tracking system 112, and thus tracking system 112 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 102 by robotic arm 114, and may capture images of the brain of patient 104 for presentation on display 110. The movement of robotic arm 114 to place external scope 116 correctly over access port 102 may be guided by tracking system 112 and the computing device in equipment tower 108. In other words, one or both of robotic arm 114 and scope 116 bear markers that are detectable by tracking system 112. As will be discussed in greater detail below, the images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

In addition to scope 116, theatre 100 can include one or more additional imaging devices. Such additional imaging devices can include, for example, ultrasound probes, Optical Coherence Tomography (OCT) probes, polarization sensitive OCT (PS-OCT) probes, micro-photo-acoustic imaging probes, spectroscopy probes (e.g. Raman or other optical spectroscopy probes, mass spectroscopy probes and the like), and the like. In the present embodiments, such imaging devices do not bear markers that are detectable by tracking system 112. These additional imaging devices can bear markers in other embodiments, however certain activities performed by the computing device in equipment tower 108 can reduce or eliminate the need for such markers on any imaging device other than scope 116.

The additional imaging devices, as well as the tools mentioned earlier (e.g. cutting tools, laser emitters and the like) can be handheld or mounted on one or more robotic arms in addition to robotic arm 114. In general, the robotic arms on which the above components are mounted are capable of movements with resolutions corresponding to the resolutions of the tools they support. Thus, for example, a laser emitter capable of targeting an area of tissue having a radius of three micrometers may be supported by a robotic arm capable of micrometer-level movements. Conversely, scope 116 may capture images of patient tissue areas of up to ten centimetres square, and thus robotic arm 114 supporting scope 116 may be capable of lower-resolution movements (e.g. millimeter-level).

Before a procedure such as that shown in FIG. 1 (which may be, for example, a tumor resection), preoperative images may be collected of patient 104, or at least of the brain or other tissues of patient 104. Such preoperative images may be collected using any of a variety of imaging modalities, including Magnetic Resonance Imaging (MRI). During the medical procedure, additional images (referred to as intraoperative images) may be collected of the brain or other tissues of patient 104, using any of the above-mentioned additional imaging devices. In general, the intraoperative images are acquired at greater pixel densities (i.e. finer resolutions) than the preoperative images, and depict smaller regions of patient 104 than the preoperative images. For example, an intraoperative ultrasound image may depict a smaller area of the brain of patient 104 than a preoperative MRI image, but at a higher resolution than the MRI image. In other words, the ultrasound image has a greater pixel density than the MRI image.

As will be described in further detail below, the computing device housed in equipment tower 108 can perform various actions to register intraoperative images captured with scope 116 and the additional imaging devices with each other and with preoperative images, thus enabling the positions of the additional imaging devices to be tracked without the need for markers visible to tracking system 112 on those imaging devices.

Figure 2:
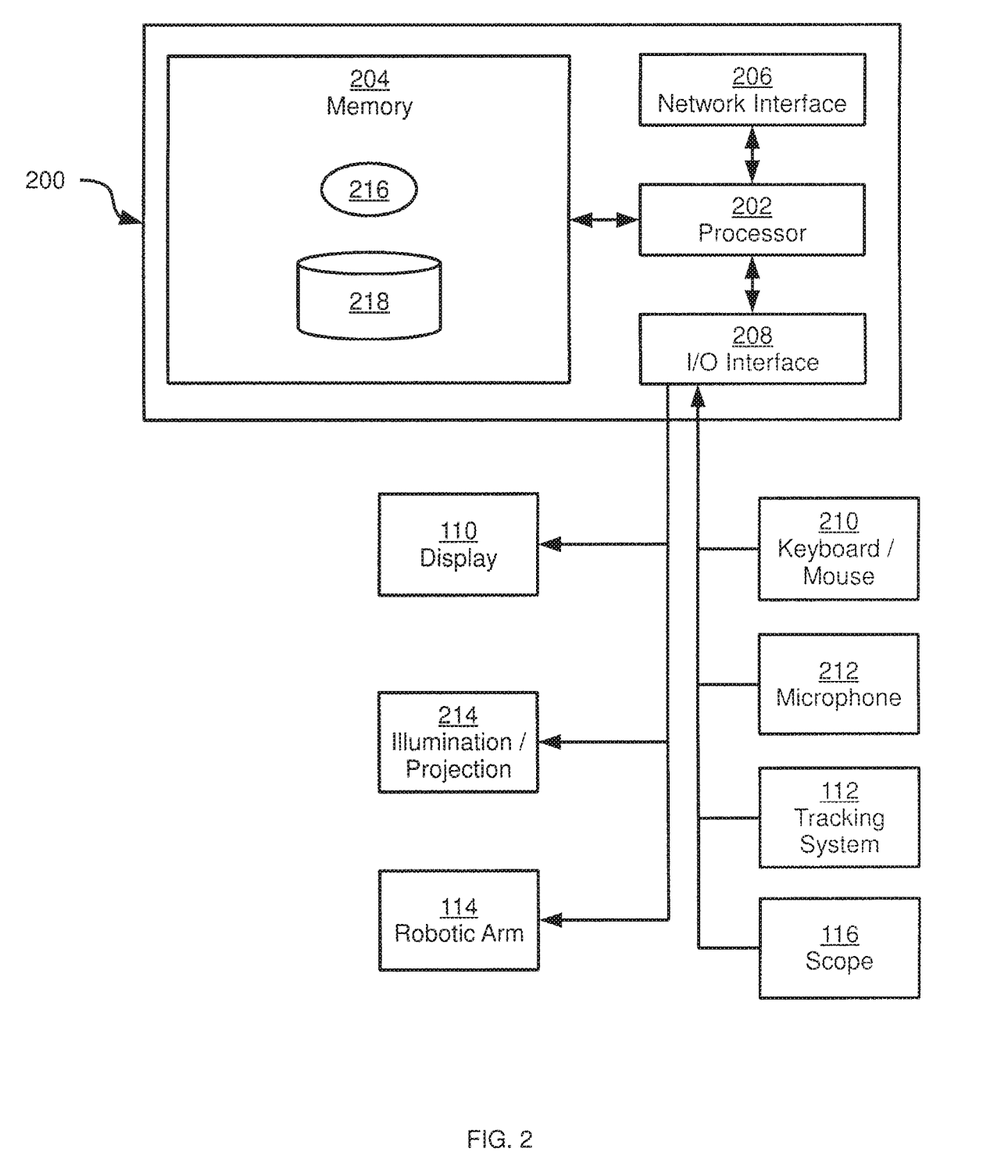
FIG. 2 depicts a computing device of the operating theatre of FIG. 1, according to a non-limiting embodiment.

Before a discussion of the functionality of the computing device, a brief description of the components of the computing device will be provided. Referring to FIG. 2, a computing device 200 is depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 also includes a network interface 206 interconnected with processor 202. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 also includes an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to input devices including a keyboard and mouse 210, a microphone 212, as well as scope 116 and tracking system 112, mentioned above. Similarly, computing device 200 can be connected to the additional imaging devices mentioned above via interface 208. Also via interface 208, computing device 200 is connected to output devices including illumination or projection components 214 (e.g. lights, projectors and the like), as well as display 110 and robotic arm 114 mentioned above. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 200 via network interface 206.

Computing device 200 stores, in memory 204, an imaging device tracking application 216 (also referred to herein as application 216) comprising a plurality of computer readable instructions executable by processor 202, When processor 202 executes the instructions of application 216 (or, indeed, any other application stored in memory 204), processor 202 performs various functions implemented by those instructions, as will be discussed below. Processor 202, or computing device 200 more generally, is therefore said to be "configured" or "operating" to perform those functions via the execution of application 216.

Also stored in memory 204 are various data repositories, including a patient data repository 218. Patient data repository 218 can contain a surgical plan defining the various steps of the minimally invasive surgical procedure to be conducted on patient 104, as well as image data relating to patient 104, such as MRI and CT scans, three-dimensional models of the brain of patient 104, and the like.

As mentioned above, computing device 200 is configured, via the execution of application 216 by processor 202, to perform various functions to capture intraoperative images depicting certain areas of patient 104 with each other and with preoperative images, in order to track the position of the above-mentioned additional imaging devices. Those functions will be described in further detail below.

Figure 3:
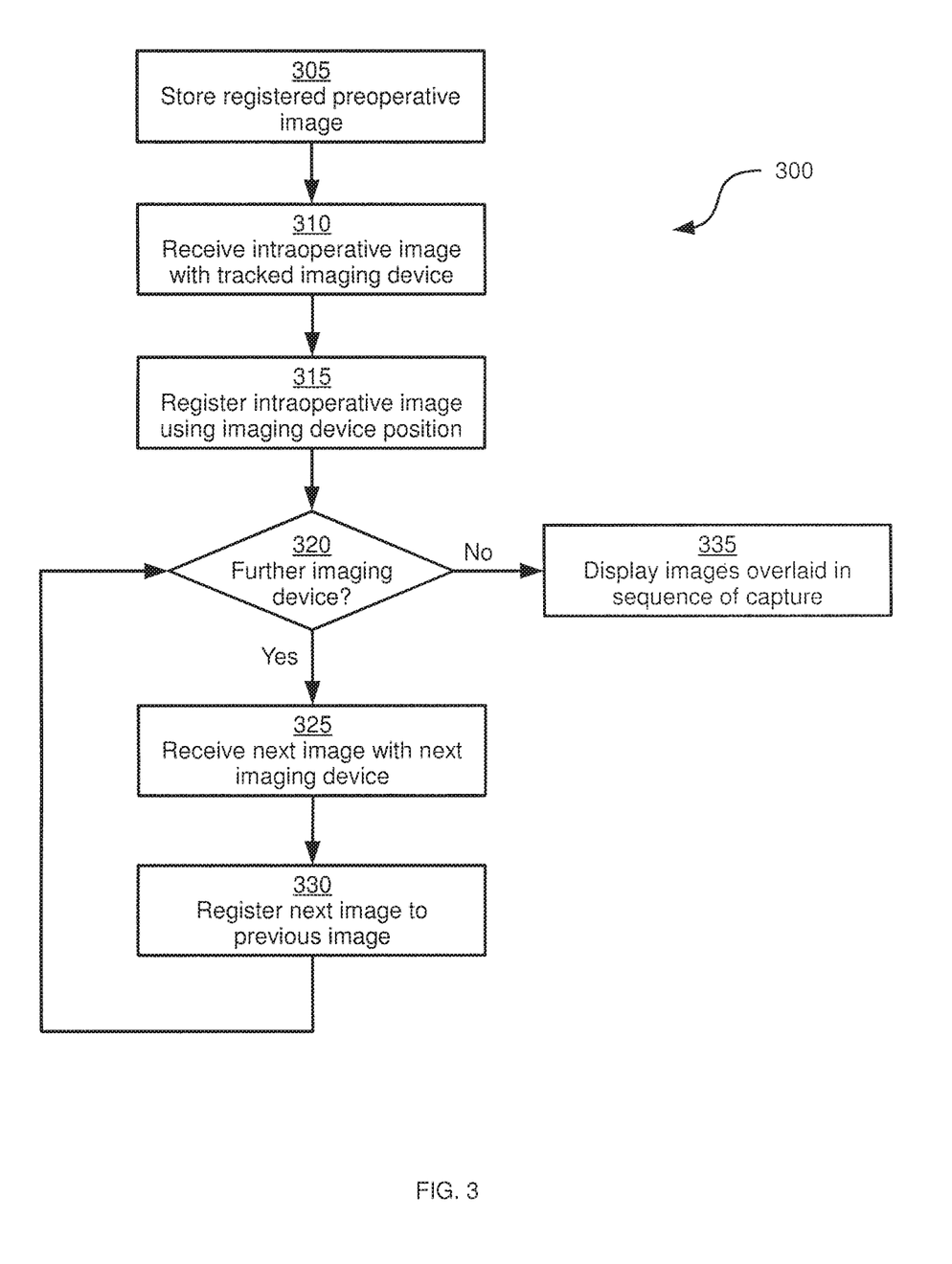
FIG. 3 depicts a method of tracking surgical imaging devices, according to a non-limiting embodiment.

FIG. 3 illustrates a method 300 of tracking surgical imaging devices. Method 300 will be described below in connection with its performance in operating theatre 100, and particularly by computing device 200. In other words, computing device 200 is configured to perform the steps of method 300 via the execution of the instructions of application 216 by processor 202.

At block 305, computing device 200 is configured to store a preoperative image of patient tissue registered to a frame of reference of a tracking system connected to the computing device. In the present example, as noted above, the patient tissue in question is the brain of patient 104. in other embodiments, the patient tissue can be any of a wide variety of other organs, tissues, portions thereof or combinations thereof.

Figure 4:
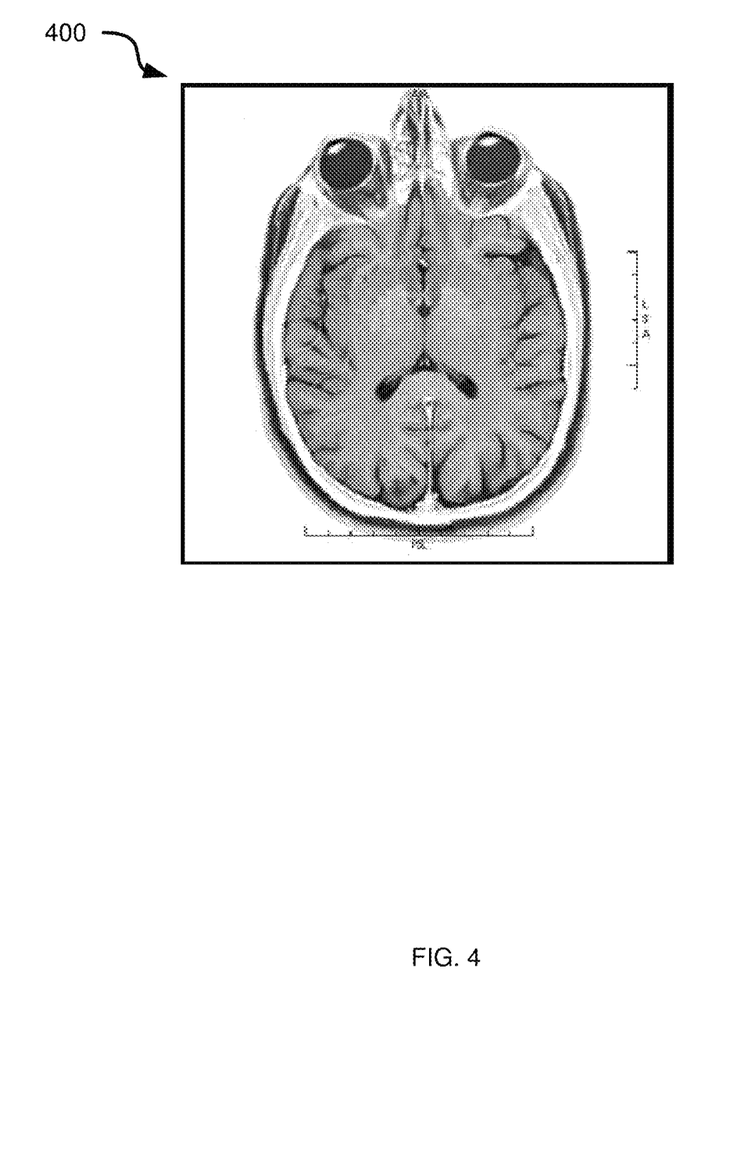
FIG. 4 depicts a preoperative image received in the method of FIG. 3, according to a non-limiting embodiment.

In the present example, the preoperative image stored at block 305 is an MRI image. The MRI image can be captured in any suitable manner (e.g. by operating an MRI scanner within or outside operating theatre 100) and provided to computing device 200 for storage at block 305 in memory 204 (e.g. in repository 218). Turning to FIG. 4, an example preoperative image 400 is shown. In the present example, image 400 depicts the entire brain of patient 104, as well as certain surrounding anatomical structures (such as the skull and eyes). This is not necessary—as noted previously, the preoperative image stored at block 305 can depict any of a wide variety of patient tissues. In addition, preoperative image 400 need not be an MRI scan. Any suitable imaging modality (e.g. computed tomography (CT), ultrasound, photo-acoustic tomography, positron emission tomography (PET) imaging and the like) can be employed to capture the image stored at block 305.

As mentioned above, the preoperative image stored at block 305 is registered to a frame of reference. In the present example, preoperative image 400 is registered to frame of reference 113 of tracking system 112. In other words, each pixel or voxel in preoperative image 400 is associated with a physical position within operating theatre 100, defined in relation to the point of origin of frame of reference 113. For example, computing device 200 can store positional data within the image file for image 400, indicating the corresponding position within frame of reference 113 for each pixel or voxel. In other embodiments, computing device 200 can store within the image file for image 400 an indication of the starting coordinates within frame of reference 113 for the first pixel or voxel of image 400, and an indication of the spacing of the pixels or voxels within frame of reference 113 (e.g. the first voxel is positioned at the coordinates 130.1 cm, 25.4 cm, 81.3 cm in frame of reference 113 and each voxel represents a distance of 0.5 mm in each axis of frame of reference 113).

The process by which preoperative image 400 is registered to frame of reference 113 is not particularly limited. For example, in some embodiments an operator (e.g. surgeon 102) can hold a tracked tool over a specific point in preoperative image 400 that corresponds to a specific location on patient 104 that bears a marker. In other words, tracking system 112 can be instructed manually of corresponding points between preoperative image 400 and patient 104.

Proceeding to block 310, during the medical procedure (that is, intraoperatively), computing device 200 is configured to receive, from a first imaging device, a first intraoperative image of a first region of the patient tissue. The image can be received by way of a control signal from computing device 200 causing the imaging device to capture the image. In other embodiments, the image can be received at computing device 200 following a command from an operator (e.g. surgeon 102) to the imaging device to capture the image.

The first intraoperative image, in general, depicts a region of the patient tissue that is smaller than the region depicted by the preoperative image. In addition, the first intraoperative image has a greater pixel density than the preoperative image (or voxel density—the term "pixel density" is used herein to indicate density of either pixels or voxels, depending on whether the relevant images are two-dimensional or three-dimensional). That is, the first intraoperative image represents a given physical area with a larger number of pixels or voxels than preoperative image 400, and thus depicts the patient tissue in the first region in greater detail than preoperative image 400.

Figure 5A:
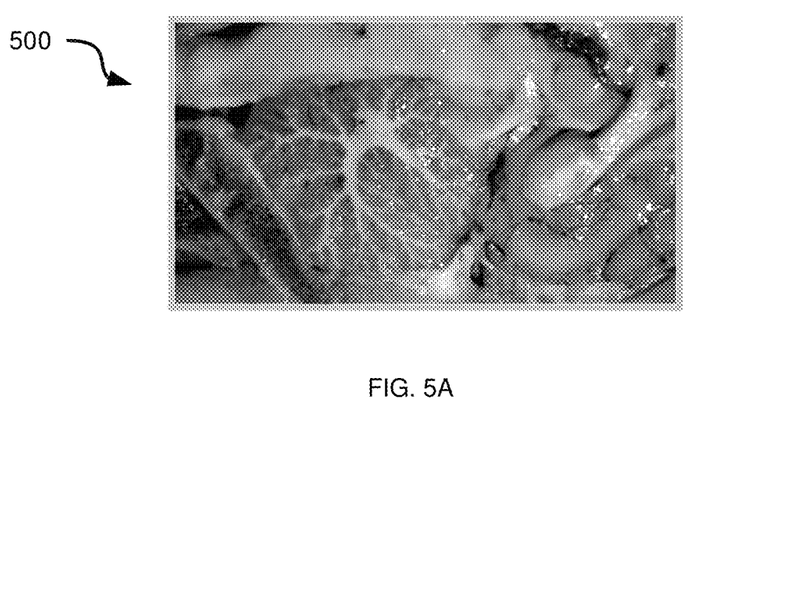
FIGS. 5A-5B depict a first intraoperative image received in the method of FIG. 3 and the registration of the first intraoperative image to the preoperative image of FIG. 4, according to a non-limiting embodiment.

Turning to FIG. 5A, an example of a first intraoperative image 500 is depicted. In particular, intraoperative image 500 is an image captured by scope 116 mounted on robotic arm 114 and provided to computing device 200.

At block 315, computing device 200 is configured to receive a position of the first imaging device (e.g. scope 116) from tracking system 112, and based on the position, to register intraoperative image 500 with frame of reference 113. Registering intraoperative image 500 with frame of reference 113 includes storing coordinates within frame of reference 113 in image 500, or (as mentioned above in connection with the registration of preoperative image 400) storing an indication of the location of the first pixel of image 500 in frame of reference 113, and an indication of the distance in frame of reference 113 between each pixel. The registration at block 315 can be performed automatically by computing device 200. For example, given that the position of scope 116 is known from tracking system 112, and given that the imaging parameters (field of view, focal length and the like) are also known, computing device 200 can determine the position of image 500 in operating theatre 100.

Figure 5B:
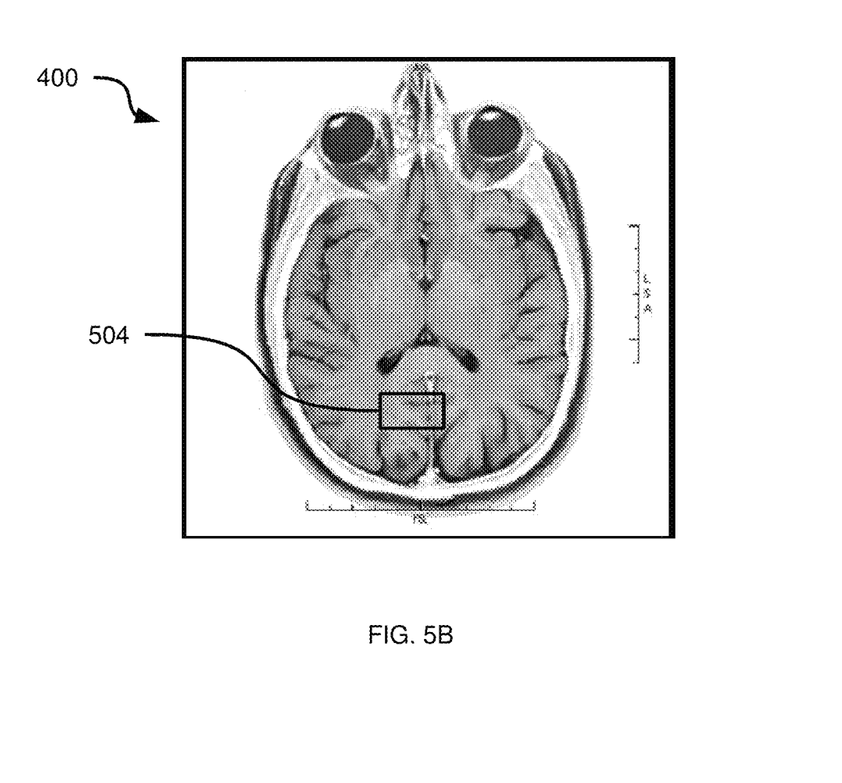

Referring to FIG. 5B, an illustration of the results of registration is provided. As noted earlier, preoperative image 400 is registered to frame of reference 113. Thus, when intraoperative image 500 is registered to frame of reference 113, it can be overlaid on preoperative image 400 to indicate what region of patient tissue is depicted by both images. In particular, FIG. 5B includes a region 504 identifying the tissue that is depicted by both images 400 and 500.

At block 320, computing device 200 is configured to determine whether any further imaging devices are active in operating theatre 100. For example, processor 202 can be configured to identify any such imaging devices that are connected to computing device 200 via interface 208. The determination can also include whether such devices are enabled (as opposed to being connected but currently disabled).

When the determination at block 320 is affirmative, the performance of method 300 proceeds to block 325. At block 325, computing device 200 is configured to receive a subsequent intraoperative image from a subsequent imaging device connected to computing device 200. As will now be apparent to those skilled in the art, the determination at block 320 can be combined with block 325, in that when an intraoperative image is received from a subsequent imaging device, the determination at block 320 is affirmative.

The subsequent intraoperative image (which may also be referred to as the second intraoperative image in the present example performance of method 300) received at block 325 depicts a subsequent region of the patient tissue (e.g. of the brain of patient 104). In general, the subsequent region is smaller than the previous region, and thus in the present performance of block 325, the region depicted in the subsequent intraoperative image is smaller than the region depicted in intraoperative image 500. In addition, the subsequent image has a greater pixel density than the previous image.

Figure 6A:
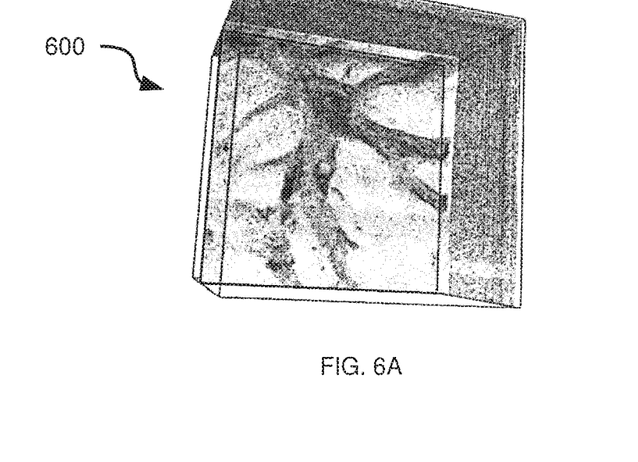
FIGS. 6A-6B depict a second intraoperative image received in the method of FIG. 3 and the registration of the second intraoperative image to the first intraoperative image of FIG. 5A, according to a non-limiting embodiment.

Turning to FIG. 6A, an example second intraoperative image 600 is depicted. In the present example, second intraoperative image 600 is captured using an OCT probe, although in other embodiments any of a wide variety of imaging devices can be employed to capture the second intraoperative image. For example, in some embodiments the second intraoperative image may be captured with another optical surgical scope, similar to scope 116 with the exception that the second scope is configured to capture higher-resolution images of smaller regions of patient tissue than scope 116.

Returning to FIG. 3, at block 330, computing device 200 is configured to register subsequent intraoperative image 600 to the previous intraoperative image (image 500, in this case). The registration of image 600 to image 500 can be conducted by computing device 200 in a variety of ways, For example, computing device 200 can employ conventional feature-based image registration techniques, intensity-based image registration techniques, or a combination thereof. In other embodiments, the above mentioned techniques can be supplemented or replaced by registration techniques such as those described in Applicant's co-pending PCT application no. PCT/CA2014/000849, filed Nov. 27, 2014 and entitled "Method, System and Apparatus for Quantitative Surgical Image Registration" which is herein incorporated by reference.

In some embodiments, further image registration techniques may be applied at block 330, such as those described in Applicant's co-pending PCT application no. PCT/CA2015/000011, filed Jan. 7, 2015 and entitled "Method, System and Apparatus for Adaptive Image Acquisition", which is herein incorporated by reference.

In further embodiments, additional image registration techniques can be employed, in addition to or instead of those mentioned above, For example, images captured with OCT or Raman spectroscopy probes can be registered to images captured with a surgical scope by detecting, within the surgical scope images, a visible pointer emitted by the OCT or Raman spectroscopy probes. The pointer (e.g. a physical pointer or a beam of light) has a known location within the probe images (based on the physical geometry of the probe itself), and thus when the pointer is detected in the scope images (i.e. a location for the pointer is established within the scope images), the probe images and scope images can be registered. More generally, each successive tool may generate light or other output that is detectable to the previous tool (even if the output is not visible to operators or to scope 116).

As another example, a probe (such as an OCT probe) may be placed in direct contact with patient tissue, the probe may cause deformation of the tissue in the form of a shallow around the probe. Computing device 200 can be configured to detect such a shallow, and register the images based on the location of the shallow (and, by implication, the location of the probe) within the scope images.

Following the completion of block 330, computing device 200 is configured to store the registered image 600 in memory 304 (for example, in repository 218). The image can be stored with registration data generated during the performance of block 330, For example, each pixel or voxel of image 600 can include positional data identifying either a corresponding location in in 500, or a position within frame of reference 113. In other examples, image 600 can contain data indicating the location within image 500 or frame of reference 113 of the first pixel of image 600, as well as the distance in image 500 or in frame of reference 113 between the pixels of image 600.

Figure 6B:
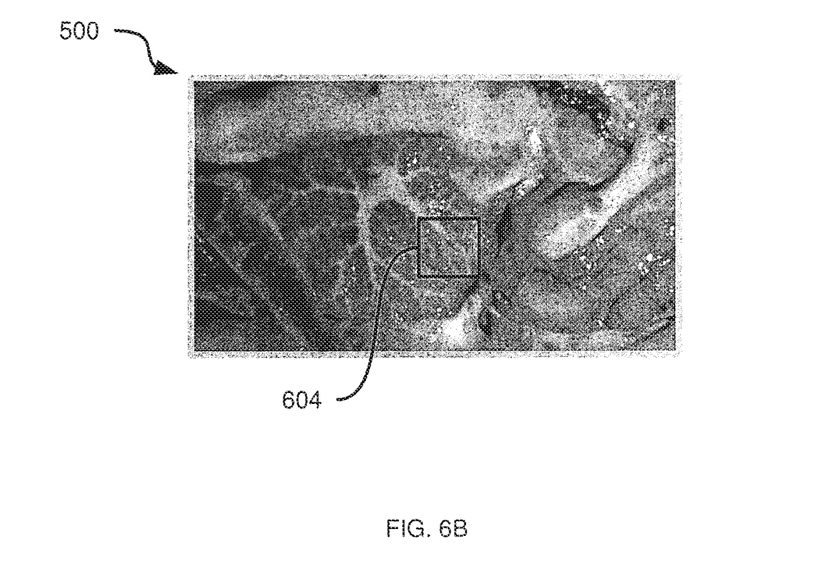

Referring to FIG. 6B, intraoperative image 500 is depicted with a subsequent region 604 of patient tissue illustrated thereon. The location and size of region 604 is determined by the registration process at block 330. As mentioned above, the image registration process at block 330 can yield position information for image 600 based on frame of reference 113, despite the fact that the subsequent imaging device is not tracked by tracking system 112 (unlike scope 116). To determine positional data for image 600, computing device 200 can be configured to register image 600 to image 500 (e.g. based on image features or other techniques as mentioned above), to derive the position of image 600 within image 500 (e.g. in terms of pixel-based coordinates). Since image 500 is already registered to frame of reference 113, the registration of image 600 to image 500 can then be converted to a registration of image 600 to frame of reference 113.

Figure 7A:
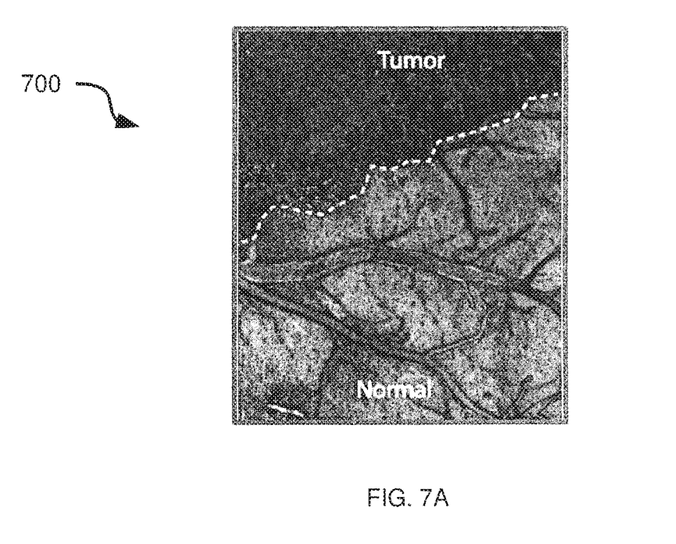
FIGS. 7A-7B depict a third intraoperative image received in the method of FIG. 3 and the registration of the third intraoperative image to the second intraoperative image of FIG. 7A, according to a non-limiting embodiment.
Figure 7B:
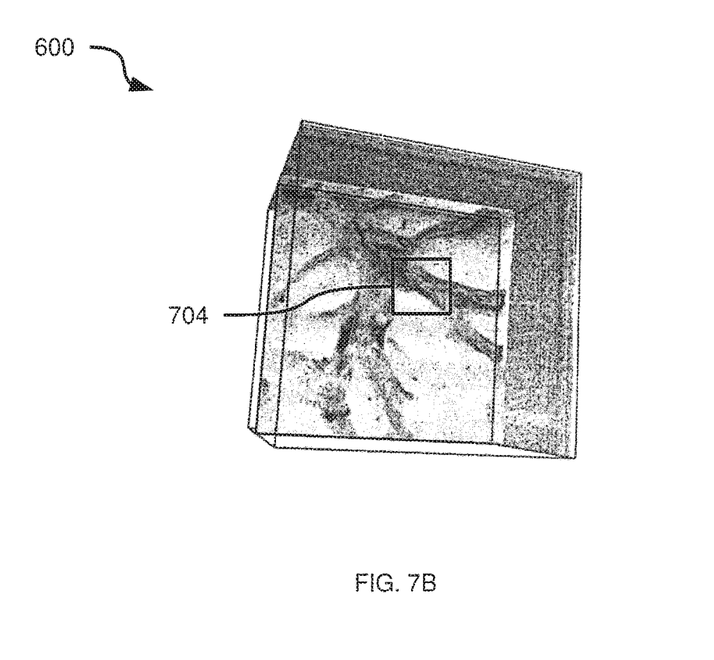

Having completed the performance of block 330, computing device 200 returns to block 320 to determine whether any further imaging devices are active. In the present example, it is assumed that the determination at block 320 is again affirmative, and through a further performance of blocks 325 and 330, a third intraoperative image 700, shown in FIG. 7A, is received at computing device from a third imaging device such as a Raman spectroscopy probe, As shown in FIG. 7B, image 700 is registered to the previous intraoperative image (image 600), and is thus determined to represent a region 704 of patient tissue smaller than the region depicted by image 600, As also seen in FIGS. 7A and s B, image 700 has a greater pixel density than image 600.

Following the second performance of blocks 325 and 330, computing device 200 again returns to block 320. In the present example it is assumed that in this third performance of block 320, the determination is negative (that is, there are no further imaging devices active). In other embodiments, the performance of blocks 325 and 330 can be repeated any number of times, depending on the imaging devices in use in operating theatre 100. Although each intraoperative image in the examples described above was captured using a different imaging modality, this is not necessary. In other performances of method 300, imaging devices using the same imaging modality (albeit it increasing pixel densities) can be employed to capture some or all of the intraoperative images.

Responsive to a negative determination at block 320, computing device 200 is configured to proceed to block 335. At block 335, computing device 200 is configured to control display 110 to present preoperative image 400, overlaid with the intraoperative images in the sequence in which they were captured. The sets of images presented at block 335 can be presented in real-time, or near real-time, as intraoperative images are received at computing device. In addition, block 335 can be performed at a later time (postoperatively, for example) by retrieving the stored registered images and presenting them on display 110 (or indeed, on any other suitable display outside operating theatre 100).

Figure 8:
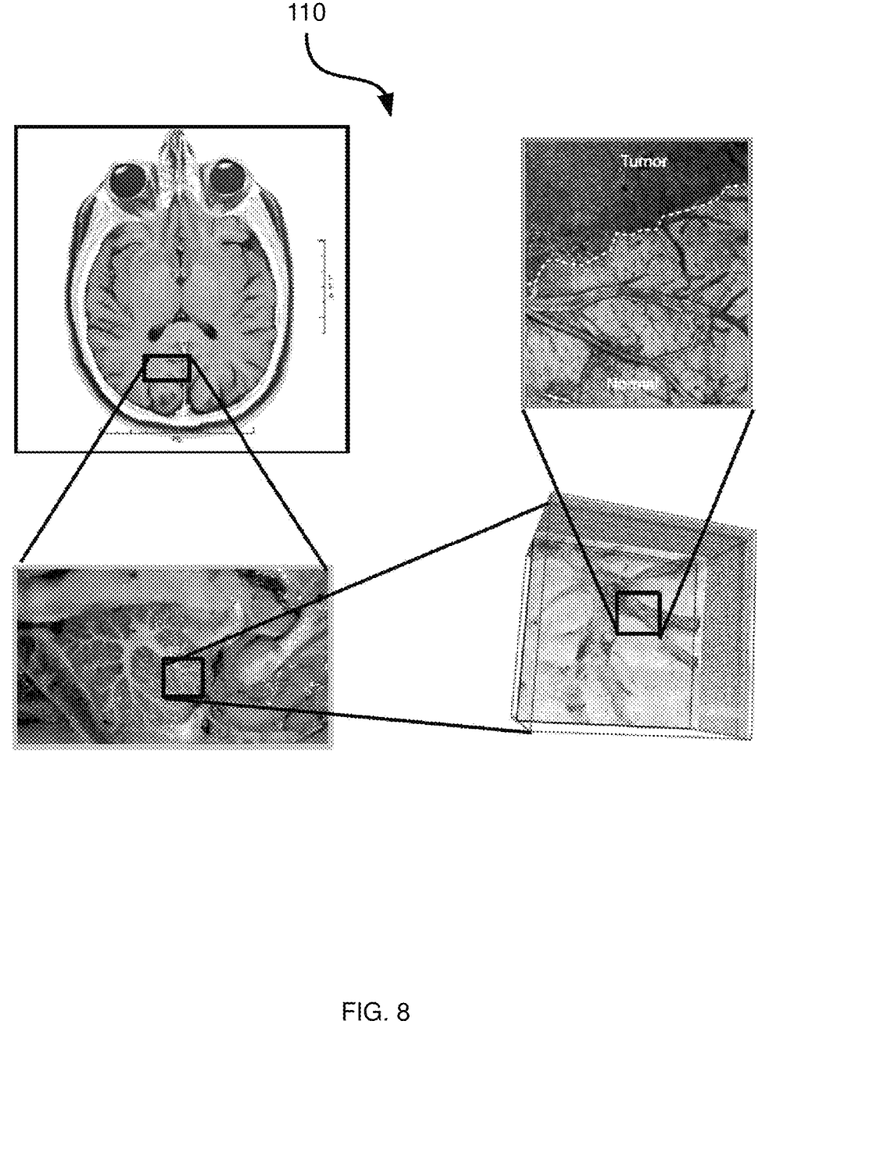
FIG. 8 depicts an example performance of block 335 of the method of FIG. 3, according to a non-limiting embodiment.

Turning to FIG. 8, an example of the sequence of images presented at block 335 is illustrated, As seen in FIG. 8, various forms of overlaying can be employed at block 335. For example, the images can be presented at different scales (as in FIG. 8), with indications such as lead lines indicating which region of one image is depicted by the next image, In other examples, all images can be shown at the same scale and the images can be overlaid directly on each other, In still other examples, the latest image (that is, the image having the highest pixel density) can be shown on display 110, and only portions of the previous images can be shown beneath the latest image.

Further operations can also be performed at block 335, or after block 335, by computing device 200. For example, computing device 200 can receive a selection of a portion of any of the images described above and shown on display 110. In response to such a selection computing device 200 can be configured to transmit a command to a robotic arm supporting a further imaging device, a tool such as a laser emitter, or the like. The command can be a command to position the instrument supported by the robotic arm at the location in frame of reference 113 corresponding to the selected portion of the image. Computing device 200 determines the location in frame of reference 113 by, as mentioned earlier, employing image registration information determined at block 330 as well as the registration of the first intraoperative image with frame of reference 113.

As will now be apparent to those skilled in the art, position data for communication to a robotic device may be derived with greater accuracy from image registration data (e.g. between images 500 and 600) than can be provided by tracking system 112. For certain surgical instruments (such as laser ablation tools, for example), such increased accuracy may be required to correctly position the instruments. A robotic positioning device, in combination with the performance of method 300, may provide such accuracy where tracking system 112 cannot. If the surgical tool or effector is at least partly controlled by a robotic arm, such increased accuracy also enables the robotic arm to limit the possible affecting area of the surgical tool. This can prevent certain important areas of the organ from being damaged unintentionally activities during the procedure.

A wide variety of other positioning devices and tools are contemplated. For example, devices such as microscopic or near-microscopic robots (also referred to as nanobots) may be employed to perform various tasks during the surgical procedure, The performance of method 300 can provide more accurate positioning information for such robots (arid any associated positioning systems used to deploy them) than tracking system 112. Examples of high-accuracy robotic positioning systems include electromagnetically-driven systems such as that described by Kummer et al., in 'OctoMag: An Electromagnetic System for 5-DOF Wireless Micromanipulation', IEEE Transactions on Robotics, 26(6) 2010. Further examples include parallel kinematic positioning devices, also referred to as hexapods (see http://www.emdt.co.uk/article/hexapods and http://biotsavart.tripod.com/hexapod.htm).

Computing device 200 can also perform the above-mentioned instruction of robotic supporting devices at block 335. For example, a selection of a location on image 500 can be received at processor 202 (e.g. from input devices such as keyboard and mouse 210), and in response computing device 200 can direct a robotic arm supporting the Raman spectroscopic probe to the selected location. Adjustments to the location of the probe before the completion of block 325 (i.e. before the capture of an image with the probe) can be performed via the receipt of control inputs at omputing device 200 from an operator such as surgeon 102.

Figure 9:
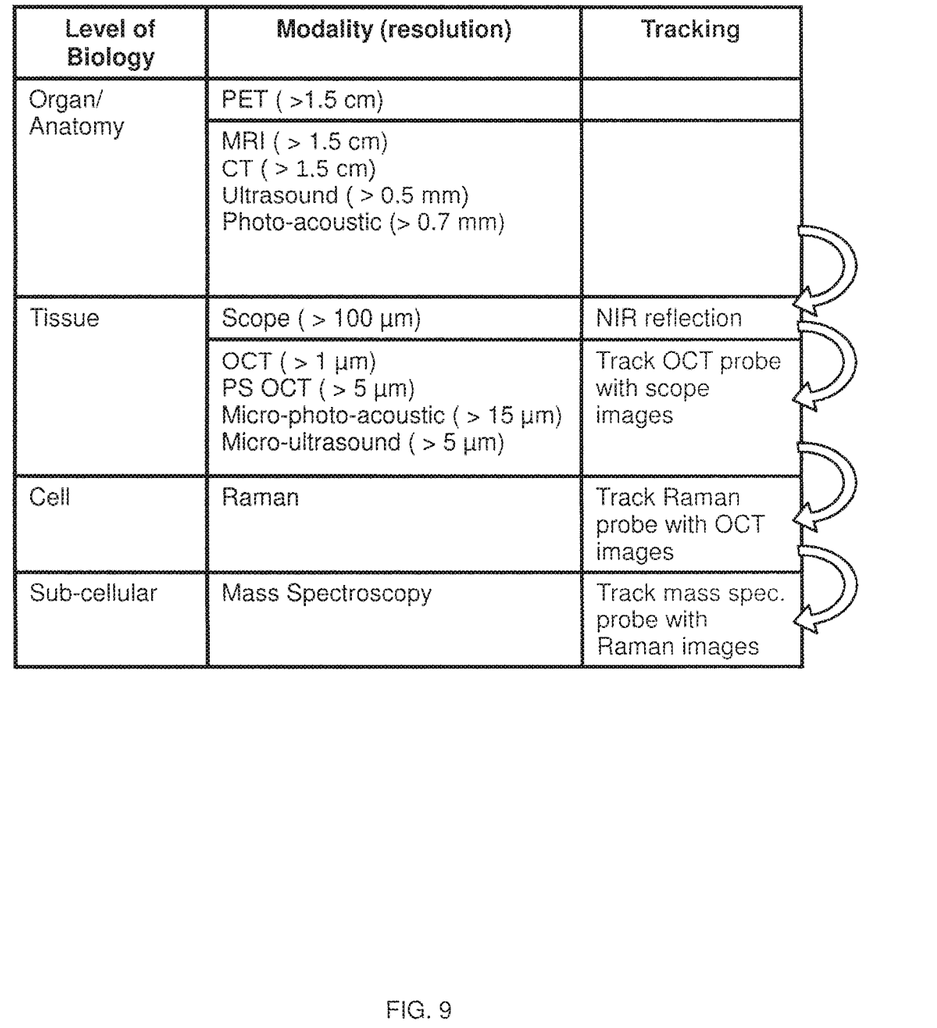
FIG. 9 depicts example imaging modalities and their levels of precision, according to a non-limiting embodiment.

FIG. 9 illustrates a sequence of imaging modalities that can be linked via the performance of method 300 during a surgical procedure. As seen in FIG. 9, successively more detailed imaging modalities (i.e. having finer resolutions) may be employed, with each modality being registered to (i.e. tracked by) the images generated by the previous modality via the performance of method 300. FIG. 9 also illustrates examples of the level of biological detailed that each modality is generally concerned with, as well as example resolutions for each modality.

Figure 10:
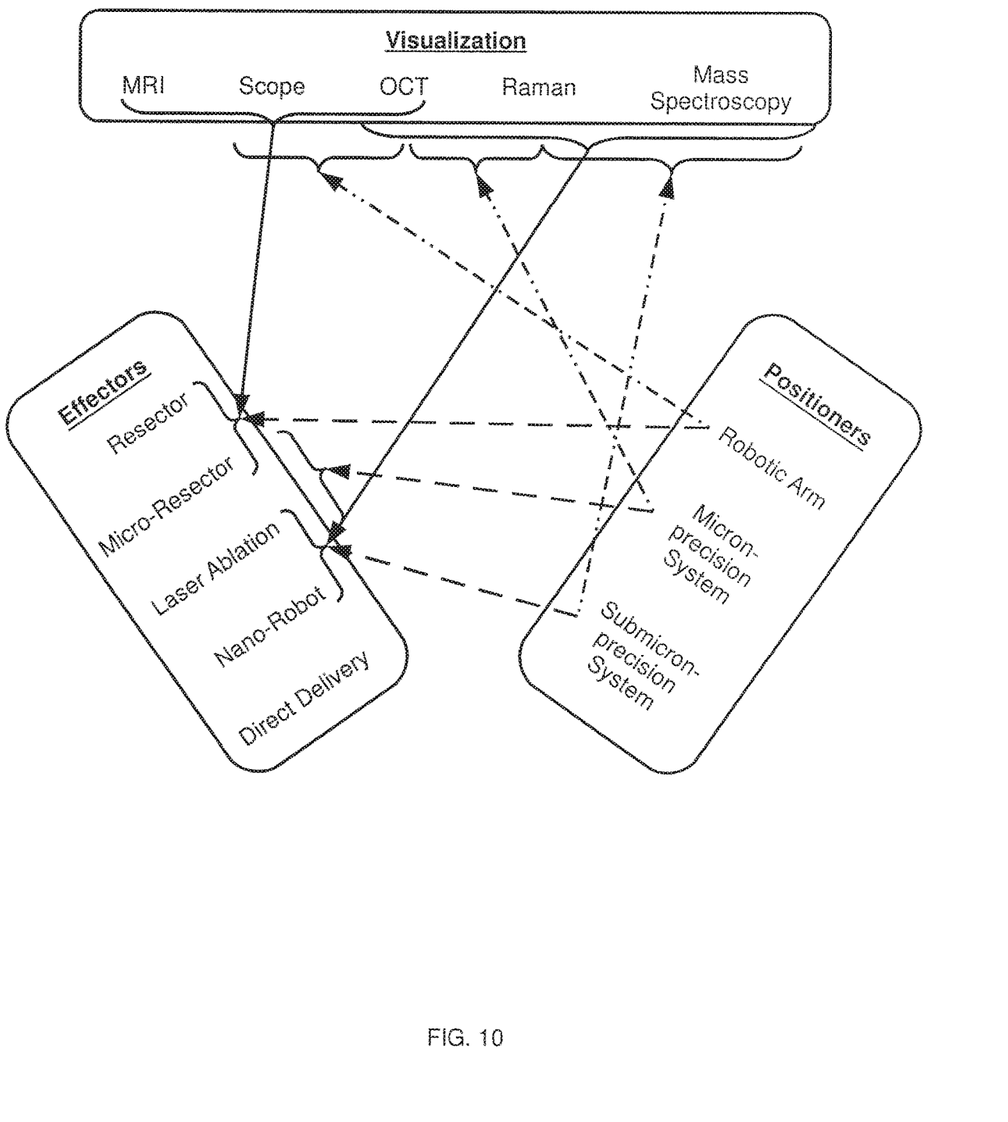
FIG. 10 depicts example relationships between visualization devices, positioning devices and effector devices, according to a non-limiting embodiment.

FIG. 10 illustrates example relationships between positioning devices (e.g. robotic arm 114), visualization devices (e.g. scope 116) and effectors (e.g. resectors and the like). As seen in FIG. 10, positioning devices can position both effectors (dashed lines) and visualization devices (dot-dashed lines), while visualization devices can provide tracking of effectors (solid lines) to provide feedback to the positioning devices, via the performance of method 300 by computing device 200.

Variations to the above-mentioned systems and methods are contemplated. For example, although individual images are described and shown in the drawings, method 300 can also be applied to video streams received at computing device 200 from imaging devices.

In some embodiments, each image (i.e,, either preoperative, intraoperative or postoperative images) captured by the system are tagged with unique identifiers, such as metadata tags, in the image header. These images are also cross-referenced and/or linked to subsequent images at various biological levels as shown in FIG. 9. These images may be stored on a local imaging database in memory 204 or remotely from computing device 200, for example on a networked picture archiving and communication system (PACS) or digital imaging and communications in medicine (DICOM) server. These images and databases may also be connected to an informatics platform where these tagged and indexed images can be used for subsequent clinical studies or procedures. Further, analytical analysis can be conducted on the databases or informatics systems to identify trends or commonalities among the different images.

Tagged and indexed images also enables the ability to match the level of accuracy between the various visualization system, imaging modalities, effector and device positioning system to maximize the effectiveness of all the tools used. Users/operators may also be able to provide feedback, comment or rate images based on quality metrics, For example, a user may rate an OCT image, using a robotic arm and a resector to provide "great wide-field view, mediocre magnification", or second image using Raman, a micron precision system and a nano-robot to provide "limited view, but excellent magnification".

The scope of the claims should not be limited by the embodiments set forth in the above examples, but should be given the broadest interpretation consistent with the description as a whole.

We claim:

1. A method of tracking positions of surgical imaging devices, using a computing device, the method comprising:
   obtaining a preoperative image of a patient, the preoperative image having a resolution;
   registering the preoperative image to a coordinate system corresponding to an operating facility;
   establishing a connection between the computing device and:
      a first imaging device having a first resolution, a first field of view, and a plurality of reflective markers;
      an optical tracking system configured to track the first imaging device in the coordinate system by detecting the plurality of reflective markers, the field of view of the optical tracking system greater than the field of view of the first imaging device; and
      a second imaging device having a second field of view, the second field of view less than the first field of view;
   receiving a first intraoperative image of a first area of the patient from the first imaging device, the first intraoperative image having a resolution finer than that of the preoperative image;
   receiving a position of the first imaging device in the coordinate system from the optical tracking system;
   receiving a second intraoperative image of a second area of the patient from the second imaging device, the second intraoperative image depicting the second area within the first area, and the second intraoperative image having a resolution finer than that of the first intraoperative image;
registering the second intraoperative image with the first intraoperative image, thereby providing a registration of the second intraoperative image with the first intraoperative image;
determining a position of the second imaging device in the coordinate system based on the registration of the second intraoperative image with the first intraoperative image;
determining whether a subsequent imaging device is detected, and
when the subsequent imaging device is detected,
   receiving a subsequent intraoperative image of a subsequent area of the patient is received from the subsequent imaging device, the subsequent intraoperative image depicting the subsequent area within a previous area, and the subsequent intraoperative image having a resolution finer than the previous intraoperative image;
   registering the subsequent intraoperative image with a previous intraoperative image, thereby providing a registration of the subsequent intraoperative image with the previous intraoperative image; and
   determining a position of the subsequent imaging device in the coordinate system based on the registration of the subsequent intraoperative image with the previous intraoperative image; and
otherwise, controlling a display to present the preoperative image overlaid with the first intraoperative image, the first intraoperative image overlaid with second intraoperative image, based on the position of the second imaging device,
the previous intraoperative image overlaid with the subsequent intraoperative image, and
each of the first intraoperative image and the second intraoperative image related to a distinct imaging modality.

2. The method of claim 1, further comprising:
establishing a connection between the computing device and a third imaging device having a third field of view, the third field of view less than the second field of view;
receiving a third intraoperative image of a third area of the patient from the third imaging device, the third intraoperative image depicting the third area within the second area, the third intraoperative image having a resolution finer than the second intraoperative image, and the third intraoperative image related to an imaging modality distinct from the first intraoperative image and the second intraoperative image;
registering the third intraoperative image with the second intraoperative image, thereby providing a registration of the third intraoperative image with the second intraoperative image; and
determining a position of the third imaging device in the coordinate system based on the registration of the third intraoperative image with the second intraoperative image, the registration of the second intraoperative image with the first intraoperative image, and the position of the first imaging device.

3. The method of claim 2, wherein receiving the first intraoperative image, receiving the second intraoperative image, and receiving the third intraoperative image respectively comprise each of the first imaging device, the second imaging device, and the third imaging device implementing a distinct imaging modality.

4. The method of claim 2, wherein registering the third intraoperative image with the second intraoperative image is based on detection of a pointer by the third imaging device in the second intraoperative image.

5. The method of claim 2,
wherein establishing the connection between the computing device and the second imaging device comprises establishing a connection between the computing device and an optical coherence tomography (OCT) probe, and
wherein establishing the connection between the computing device and the third imaging device comprises establishing a connection between the computing device and a spectroscopic probe.

6. The method of claim 1, further comprising registering the first intraoperative image with the preoperative image by identifying corresponding image features in the first intraoperative image and the preoperative image.

7. The method of claim 1, wherein obtaining the preoperative image comprises obtaining an MRI image.

8. The method of claim 1, further comprising:
receiving a selection of a location within the second intraoperative image; and
determining a position of the selected location within the coordinate system based on the registration of the second intraoperative image with the first intraoperative image.

9. The method of claim 1, wherein establishing the connection between the computing device and the first imaging device the comprises establishing a connection between the computing device and an optical scope.

10. The method of claim 1, further comprising establishing a connection between the computing device and a remote imaging database, the remote imaging database operable with at least one of a networked picture archiving and communication system (PACS) and a digital imaging and communications in medicine (DICOM) server.

11. The device of claim 1, wherein the processor is configured to establish a connection between the computing device and a remote imaging database, the remote imaging database operable with at least one of a networked picture archiving and communication system (PACS) and a digital imaging and communications in medicine (DICOM) server.

12. A computing device, comprising a processor configured to:
obtain a preoperative image of a patient, the preoperative image having a resolution;
register the preoperative image to a coordinate system corresponding to an operating facility;
establish a connection between the computing device and:
   a first imaging device having a first resolution, a first field of view, and a plurality of reflective markers;
   an optical tracking system configured to track the first imaging device in the coordinate system by detecting the plurality of reflective markers, the field of view of the optical tracking system greater than the field of view of the first imaging device; and
   a second imaging device having a second field of view, the second field of view less than the first field of view;
receive a first intraoperative image of a first area of the patient from the first imaging device, the first intraoperative image having a resolution finer than that of the preoperative image;
receive a position of the first imaging device in the coordinate system from the optical tracking system;

receive a second intraoperative image of a second area of the patient from the second imaging device, the second intraoperative image depicting the second area within the first area, and the second intraoperative image having a resolution finer than that of the first intraoperative image;

register the second intraoperative image with the first intraoperative image, thereby providing a registration of the second intraoperative image with the first intraoperative image;

determining a position of the second imaging device in the coordinate system based on the registration of the second intraoperative image with the first intraoperative image;

determine whether a subsequent imaging device is detected, and when the subsequent imaging device is detected,
  receive a subsequent intraoperative image of a subsequent area of the patient is received from the subsequent imaging device, the subsequent intraoperative image depicting the subsequent area within a previous area, and the subsequent intraoperative image having a resolution finer than the previous intraoperative image;
  register the subsequent intraoperative image with a previous intraoperative image, thereby providing a registration of the subsequent intraoperative image with the previous intraoperative image; and
  determine a position of the subsequent imaging device in the coordinate system based on the registration of the subsequent intraoperative image with the previous intraoperative image; and
  otherwise, control a display to present the preoperative image overlaid with the first intraoperative image, the first intraoperative image overlaid with second intraoperative image, based on the position of the second imaging device,
  the previous intraoperative image overlaid with the subsequent intraoperative image, and
  each of the first intraoperative image and the second intraoperative image related to a distinct imaging modality.

13. The computing device of claim 12, wherein the processor is further configured to:
  establish a connection between the computing device and a third imaging device having a third field of view, the third field of view less than the second field of view;
  receive a third intraoperative image of a third area of the patient from the third imaging device, the third intraoperative image depicting the third area within the second area, the third intraoperative image having a resolution finer than the second intraoperative image, and the third intraoperative image related to an imaging modality distinct from the first intraoperative image and the second intraoperative image;
  register the third intraoperative image with the second intraoperative image, thereby providing a registration of the third intraoperative image with the second intraoperative image; and
  determine a position of the third imaging device in the coordinate system based on the registration of the third intraoperative image with the second intraoperative image, the registration of the second intraoperative image with the first intraoperative image, and the position of the first imaging device.

14. The device of claim 13, wherein the processor is configured to respectively receive the first intraoperative image, receive the second intraoperative image, and receive the third intraoperative image from each of the first imaging device, the second imaging device, and the third imaging device implementing a distinct imaging modality.

15. The device of claim 13, wherein the processor is configured to register the third intraoperative image with the second intraoperative image based on detection of a pointer by the third imaging device in the second intraoperative image.

16. The device of claim 12, wherein the processor is configured to establish the connection between the computing device and the first imaging device by establishing a connection between the computing device and an optical scope.

17. The device of claim 13,
  wherein the processor is configured to establish the connection between the computing device and the second imaging device by establishing a connection between the computing device and an optical coherence tomography (OCT) probe, and
  wherein the processor is configured to establish the connection between the computing device and the third imaging device by establishing a connection between the computing device and a spectroscopic probe.

18. The device of claim 12, wherein the processor is further configured to register the first intraoperative image with the preoperative image by identifying corresponding image features in the first intraoperative image and the preoperative image.

19. The device of claim 12, wherein the processor is configured to obtain the preoperative image by obtaining an MRI image.

20. The device of claim 12, wherein the processor is further configured to:
  receive a selection of a location within the second intraoperative image; and
  determine a position of the selected location within the coordinate system based on the registration of the second intraoperative image with the first intraoperative image.

* * * * *